US008692993B2

(12) United States Patent
Mendele et al.

(10) Patent No.: US 8,692,993 B2
(45) Date of Patent: Apr. 8, 2014

(54) OPTICAL FLOW CYTOMETER AND METHOD OF INVESTIGATION

(75) Inventors: Bálint Tibor Mendele, Budapest (HU); Attila Zsolt Tremmel, Siófok (HU); Péter Tóth-Miklós, Budapest (HU); Péter Kovács, Szentendre (HU); László Lehel Laczó, Budapest (HU); Miklós Zsolt Svarcz, Pomáz (HU)

(73) Assignee: Diatron MI ZRT., Budapest (HU)

( * ) Notice: Subject to any disclaimer, the term of this patent is extended or adjusted under 35 U.S.C. 154(b) by 456 days.

(21) Appl. No.: 13/124,083

(22) PCT Filed: Oct. 13, 2009

(86) PCT No.: PCT/HU2009/000086
§ 371 (c)(1),
(2), (4) Date: Jun. 30, 2011

(87) PCT Pub. No.: WO2010/043917
PCT Pub. Date: Apr. 22, 2010

(65) Prior Publication Data
US 2011/0256523 A1    Oct. 20, 2011

(30) Foreign Application Priority Data

Oct. 13, 2008  (HU) .................................... 0800614

(51) Int. Cl.
*G01N 21/00* (2006.01)
*G01N 33/48* (2006.01)
*G01N 31/00* (2006.01)
*G01N 21/03* (2006.01)

(52) U.S. Cl.
USPC ................. 356/337; 356/39; 436/17; 436/63; 436/165

(58) Field of Classification Search
USPC .............. 356/39–41, 73, 335–343; 435/3, 29, 435/286.2; 436/63
See application file for complete search history.

(56) References Cited

U.S. PATENT DOCUMENTS

| 4,683,212 A | 7/1987 | Uffenheimer |
| 4,983,038 A | 1/1991 | Ohki et al. |

(Continued)

FOREIGN PATENT DOCUMENTS

| EP | 0718619 A2 | 6/1996 |
| WO | 9958955 A1 | 11/1999 |

(Continued)

*Primary Examiner* — Gregory J Toatley
*Assistant Examiner* — Willie Merrell, II
(74) *Attorney, Agent, or Firm* — Fitch, Even, Tabin & Flannery LLP

(57) ABSTRACT

The present invention relates to a flow cytometer (10) for in vitro assaying of human or animal whole blood and to an investigation method using the flow cytometer. Enhanced detection properties are achieved by it relative to the prior art cytometers of the same kind. Here, automated beam positioning is also solved. To these ends, collection of light scattered by the cellular components of human or animal whole blood and its transmission to suitable optical sensing elements take place by a coupling member with a particular end construction, in particular through one or more optical fiber bundles. Preparation of a blood sample for the assay, that is, mixing up said human or animal whole blood with appropriate reagents is performed by a hydro-pneumatical unit (12) of a particular design. Moreover, the actual assaying takes place in a flow cell (22) of a particular construction, which assists to improve the signal-to-noise ratio of the present flow cytometer.

28 Claims, 8 Drawing Sheets

(56) References Cited

U.S. PATENT DOCUMENTS

| | | |
|---|---|---|
| 5,461,475 A | 10/1995 | Lerner et al. |
| 5,461,476 A | 10/1995 | Fournier |
| 5,488,469 A | 1/1996 | Yamamoto et al. |
| 5,631,730 A | 5/1997 | Chupp et al. |
| 5,679,575 A * | 10/1997 | Kubota et al. .................. 436/49 |
| 5,895,764 A | 4/1999 | Sklar et al. |
| 6,228,652 B1 * | 5/2001 | Rodriguez et al. ............. 436/63 |
| 6,798,508 B2 | 9/2004 | Kramer |
| 7,113,266 B1 | 9/2006 | Wells |
| 2002/0192113 A1 | 12/2002 | Uffenheimer et al. |
| 2003/0054558 A1 | 3/2003 | Kurabayashi et al. |
| 2004/0036874 A1 | 2/2004 | Kramer |

FOREIGN PATENT DOCUMENTS

| | | |
|---|---|---|
| WO | 0194938 A1 | 12/2001 |
| WO | 2004018967 A1 | 3/2004 |

\* cited by examiner

OPTICAL FLOW CYTOMETER AND METHOD OF INVESTIGATION

CROSS REFERENCE TO RELATED APPLICATION

This application is the National Stage filing under 35 U.S.C. 371 of International Application No. PCT/HU2009/000086, filed Oct. 13, 2009, and claims priority of Hungarian Patent Application No. P0800614 filed Oct. 13, 2008, the subject matter of which in its entirety, is incorporated herein by reference

BACKGROUND OF THE INVENTION

The present invention is an optical flow cytometer, in particular an optical hematology analyser instrument with enhanced detection properties for in vitro analysis of the formed elements of human or animal whole blood. The invention also relates to an assaying process that exploits the optical flow cytometer itself.

In the field of diagnostical analysis of samples derived from humans and animals, cytometry looks back to a history of several decades. Flow cytometry and flow cytometers is/are a laboratory technique/devices apt for a rapid multi-parametric assaying of cells. By means of these, each cell type within a mixed cell population can be particularly detected, analysed and separated based on their phenotype or functional state. The flow cytometers used nowadays determine a part of the parameters through optical based measurements. The techniques that are based on the analysis of scattered or absorbed polarised light are often used to determine the populations of the cellular components. Such a solution is discussed e.g. in U.S. Pat. No. 7,113,266. Moreover, by means of an optical based measurement, the largeness and the granularity of various formed elements (i.e. red blood cells, blood platelets, white blood cells, such as lymphocytes, monocytes, granulocytes, etc.) of a given sample, provided particularly in the form of a human or animal whole blood sample, can be measured simultaneously.

According to the commonly used optical based measurement (in this regard be referred to International Publication Pamphlet Nos. WO99/58955 A1 and WO01/94938 A1), at first the blood sample to be assayed (or a portion thereof) is mixed manually or in an automated manner with appropriate reagents under certain ambient conditions, generally within separate chambers, thereby preparing different sample solutions from said sample in the chambers each. To achieve a more precise separation of the populations, said biochemical preparation of the blood sample cannot be divided off the measurement. The thus obtained sample solutions are each directed through a so-called flow cell (or cuvette) formed preferably with a thin and straight flow passage. In the meantime, said sample solution flowing through the cell is illuminated in an illumination zone in a direction essentially perpendicular to the flow direction by one or more laser lights of a certain wavelength (single-channel/multichannel analysis). The laser light scattered by the formed elements passing through the passage of the flow cell with the sample solution is detected by appropriate sensing element(s) (for example by means of photodetectors, photoelectron multipliers, etc.) in one or more different conical angle ranges. The detected signals are then analysed by means of appropriate algorithms and as a result of the analysis pieces of information concerning the formed elements (cells) of the sample assayed are generated. In a part of the assays done, sensing is performed in a low-angle range and in a high-angle range through exploiting laser light scattered by the various cells. The electronical signal obtained through sensing the laser light coming from the low-angle range is proportional to the size of the cells in the blood sample, while the electronical signal detected in the high-angle range is proportional to the internal granularity of said cells of the blood sample. As the power of the illuminating laser light is significantly higher than that of the laser light scattered by the formed elements, there is an attempt to decrease the portion of the illuminating laser light that reaches the detector(s) directly, i.e. without being scattered by the formed elements of the sample, by various techniques.

In certain cases, the scattered laser light is collected by means of an optical fiber bundle. In these cases, the efficiencies of the couplings into and out of said optical fibers are of extreme importance. Such a solution is discussed e.g. in U.S. Pat. No. 6,798,508, wherein the light incoupling ends of elementary optical fibers of an optical fiber bundle are mounted into holes formed circularly within a concave support element and face into the direction of the illumination zone. Moreover, to achieve higher illumination of said light incoupling ends of the elementary optical fibers, collecting lenses are arranged in the path of the scattered laser light in front of said light incoupling ends, as is disclosed in U.S. Pat. No. 5,461,476.

To perform cytometric assays with an adequate precision, the sample to be assayed must be focused during its passing through the passage of the flow cell. In most cases, to this end the so-called hydrodinamical focusing is applied. The burden of this is that said sample is fed in a suitable arrangement into a laminarly flowing liquid (the so-called sheath liquid) before it enters the passage of the flow cell: the sample is introduced into the sheath liquid through a sample feeding needle that is arranged along the geometrical axis of a conical throat formed in the flow path upstream of said cell at a flow rate corresponding basically to that of the sheath liquid. As a result of this, a sample flow with a cross section being smaller than that of the passage of said flow cell is produced. In general, a continuous flow of the sheath liquid and the sample solution is maintained by means of pumps, as it is detailed in U.S. Pat. No. 5,895,764. Due to the hydrodinamical focusing and the laminar flow, the formed elements are advancing all along the center of the flow cross section, within a "liquid tube" with an inner diameter of several tens of microns in the sample flow. The "following distance" of the cells in said sample flow can be set by adjusting the degree of dilution of the sample. By means of applying an adequate degree of dilution, it can be achieved that the formed elements of the assayed sample pass through the illumination zone essentially one by one in the sample solution. Consequently, every formed element of the sample solution is illuminated essentially to the same extent.

In light of the above, the object of the present invention is to provide an optical based flow cytometer that consists of, as far as its main subunits are concerned, subunits that are developed compared to the cytometers used nowadays in the clinical practice based on similar operating principles.

In particular, the aim of the present invention is to attain an optical based flow cytometer, wherein a relatively small amount of laser light used to illuminate cellular components of the sample reaches directly the sensing element(s).

A further aim of the present invention is to accomplish a flow cytometer, wherein the laser light scattered by cellular components in a sample to be assayed is collected and sensed at a very high efficiency and with no engineering compromises.

A yet further object of the present invention is to achieve a flow cytometer that comprises a hydro-pneumatic biochemical sample preparation unit of enhanced efficiency for the more reliable and precise separation of the different cell populations.

Flawless and trouble-free measurements require a flow cytometer that operates in a stable manner. Thus, there is a need for the optical elements to be adjusted regularly during the whole service life of said cytometer. In case of cytometers commonly used in clinical practice, said adjustment is generally performed manually. This, however, requires high competence and the quality of adjustment highly depends on the skills of the operator actually performing the adjustment. Such a solution with manually effected adjustment is disclosed e.g. in U.S. Pat. No. 5,631,730. According to this, an approximate positioning of the illuminating beam onto the illumination zone takes place by means of mirrors arranged in the path of said beam (coarse-positioning), while an accurate lateral adjustment of said beam within the illumination zone is performed by changing the distance between individual prisms of a pair of small angle prisms arranged in the path of said beam (fine-positioning). Hence, a yet further aim of the present invention is to provide a flow cytometer that performs the adjustment of the optical elements, such as e.g. the positioning of the beam spot of the illuminating laser light (if necessary) from time to time automatically with no intervention of operators.

A yet further aim of the present invention is to provide an optical flow cytometer suitable for performing automatic ratings in the sense whether or not the intensity of a laser beam used for the illumination is uniform within a given measuring accuracy in a certain cross-section perpendicular to the direction of propagation, or the optical path is clear enough.

Moreover, a yet further object of the present invention is to provide an optical inspection method which by exploiting the flow cytometer according to the present invention forms an efficient and automated method of inspection for the study of cellular components of a liquid phase sample.

In light of the above, the above objects aiming at the provision of an optical flow cytometer are achieved by the flow cytometer according to claim 1. Further preferred embodiments of said optical flow cytometer are set forth in claims 2 to 17. In light of the above, the above objects aiming at providing an investigation method are achieved by the optical method of investigation specified by claim 18. Further preferred embodiments of said investigation method are defined by claims 19 to 28.

In what follows, the invention is discussed in more detail with reference to the following drawings, wherein FIG. 1 is a block diagram of a possible embodiment of the optical flow cytometer according to the invention—here, n denotes the number of branches of the hydro-pneumatical unit of said embodiment, while p stands for the number of light offtake bundles (and, hence, of detection conical angle ranges);

Figure 1:
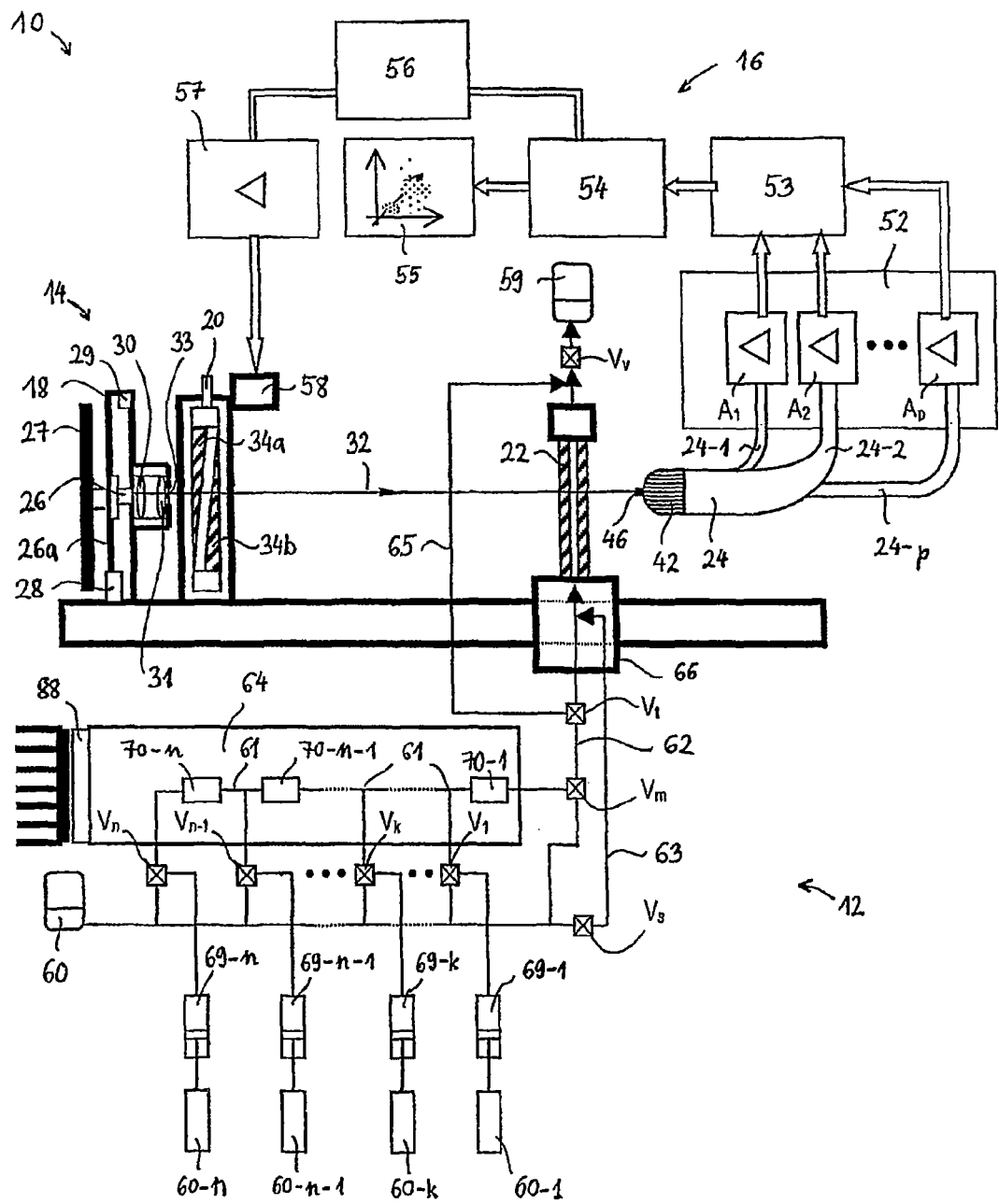
Figure 2:
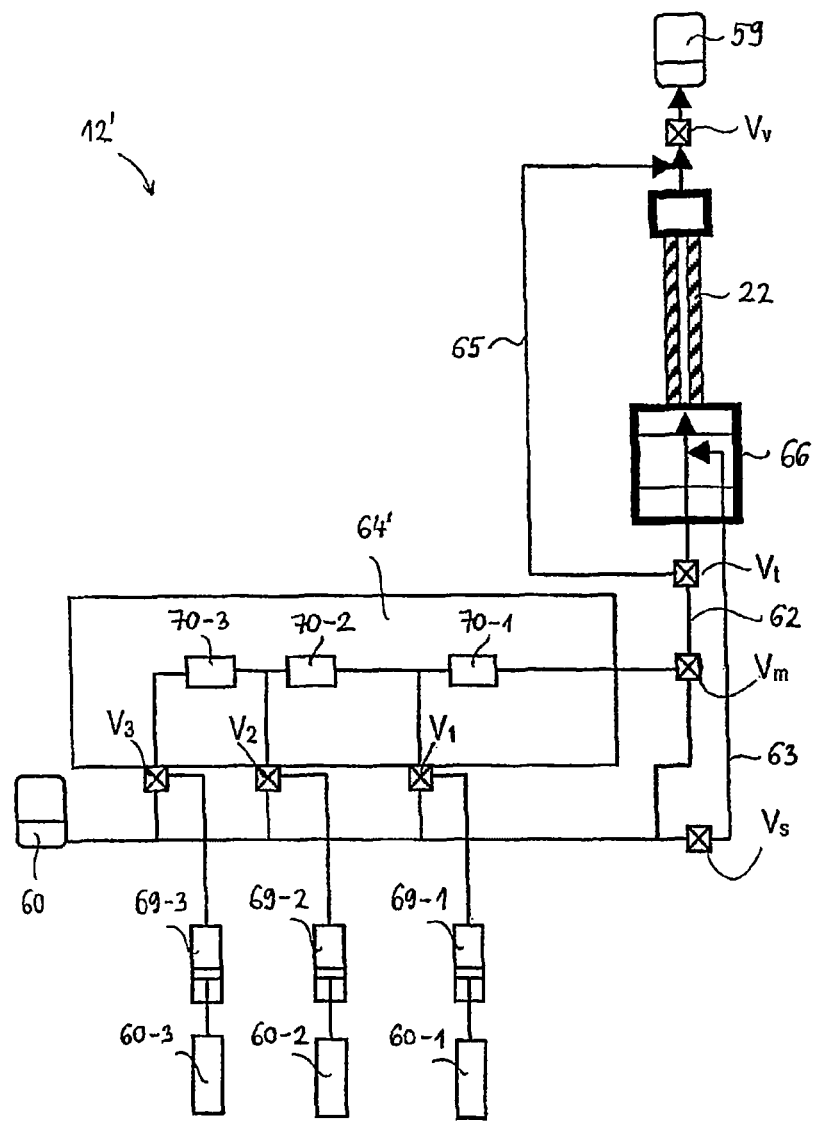
FIG. 2 is a block diagram of a possible embodiment of the hydro-pneumatical unit shown in FIG. 1, wherein said embodiment comprises three reagent branches (the sample solution consisting of whole blood and an isotonic diluent, the hemolysing agent and the stabilizing agent)
Figure 4A:
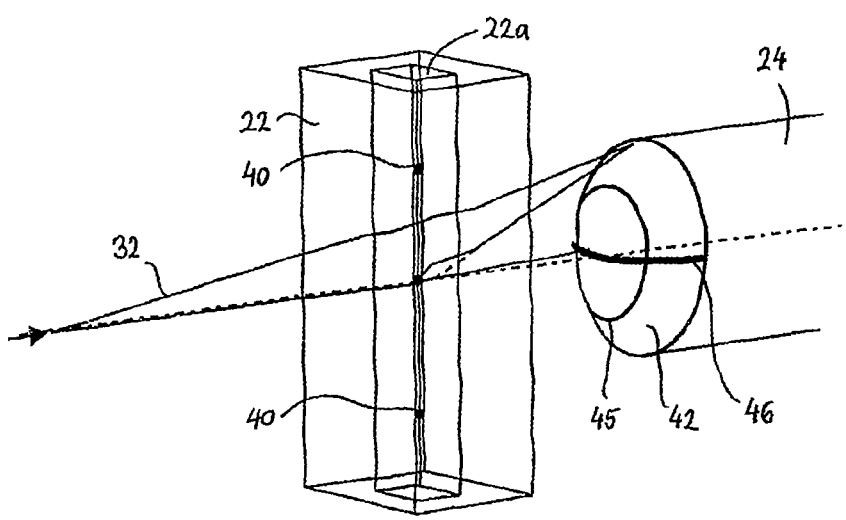
FIG. 4A is a perspective view of the light incoupling end of a light collecting optical fiber bundle used in the optical unit of the flow cytometer according to the invention.
Figure 4B:
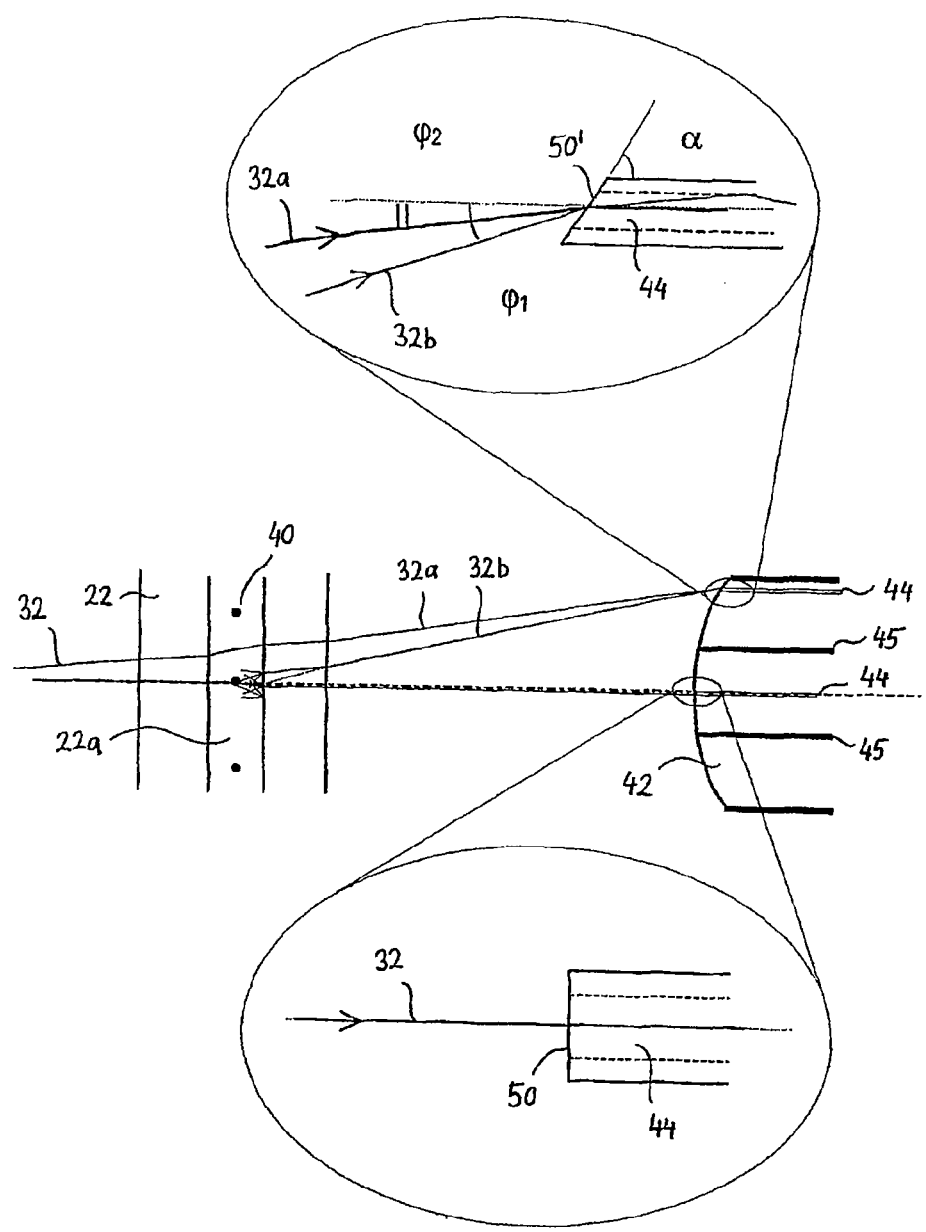
Figure 5A:
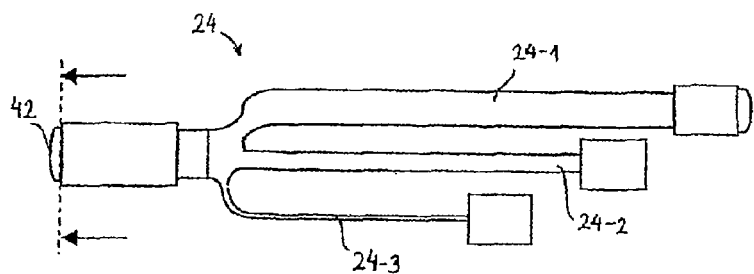
Figure 5B:
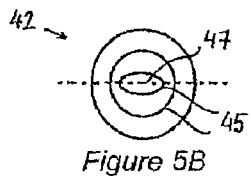
Figure 5C:
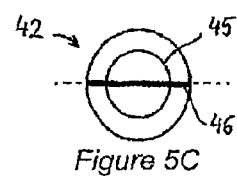
Figure 6A:
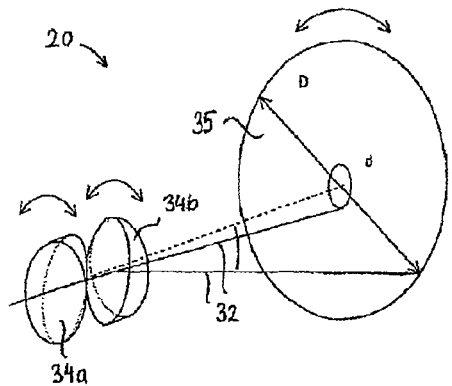
Figure 6B:
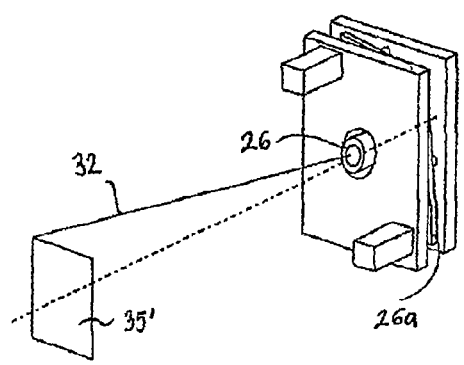
Figure 7A:
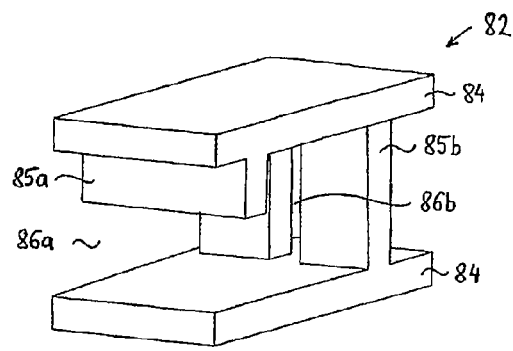
Figure 7B:
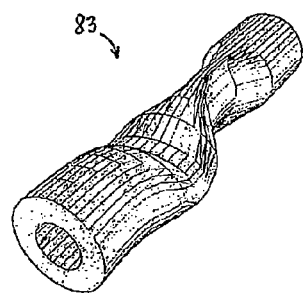
Figure 7C:
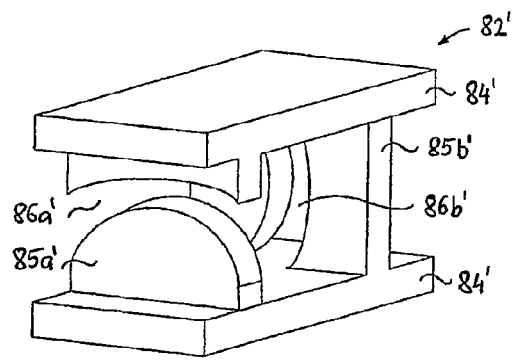
Figure 7D:
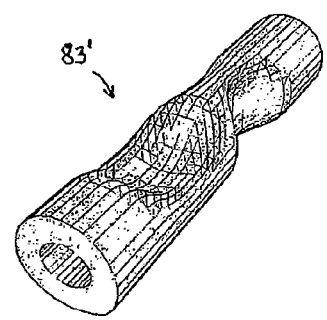
Figure 8:
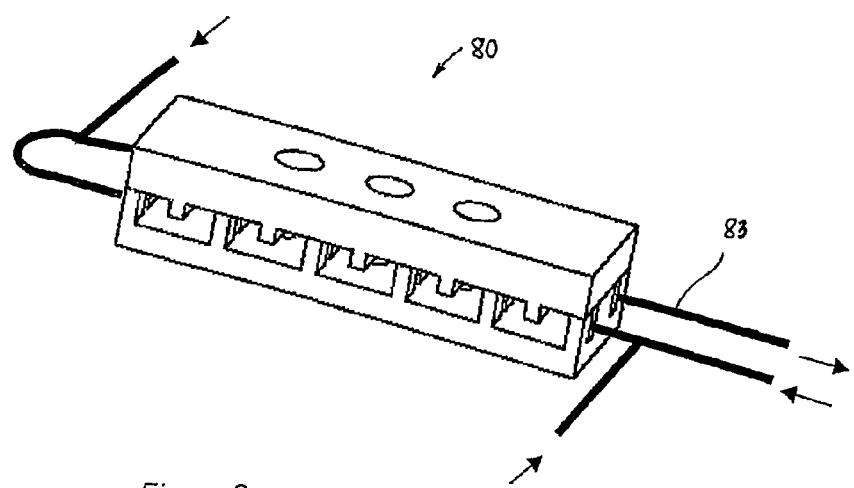
Figure 9:
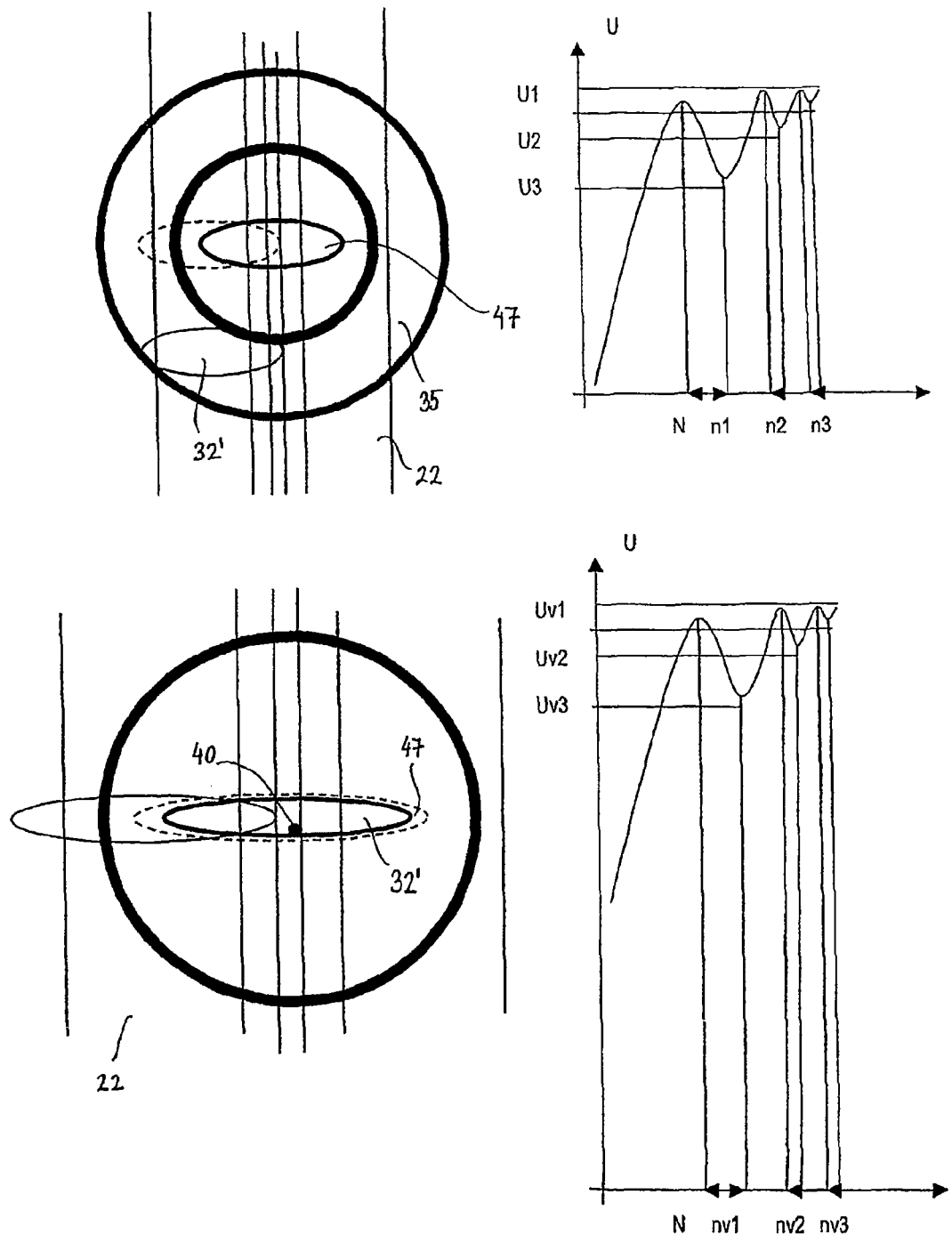
Figure 10A:
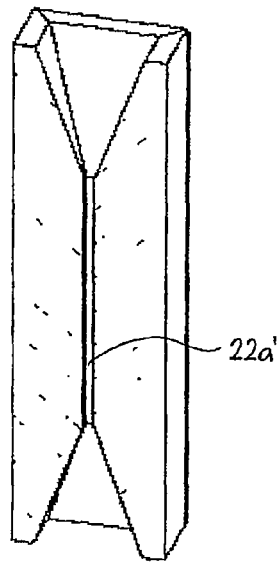
Figure 10B:
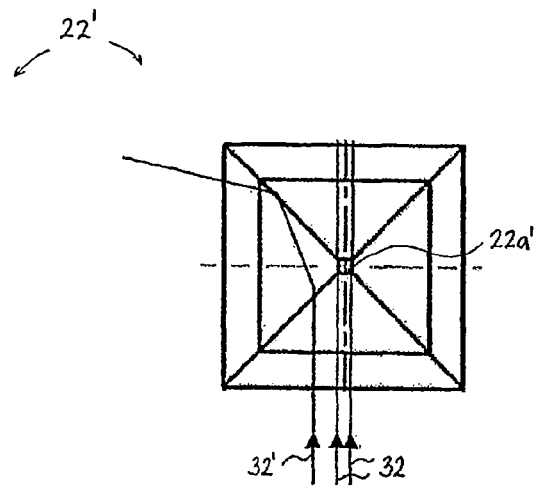
Figure 11A:
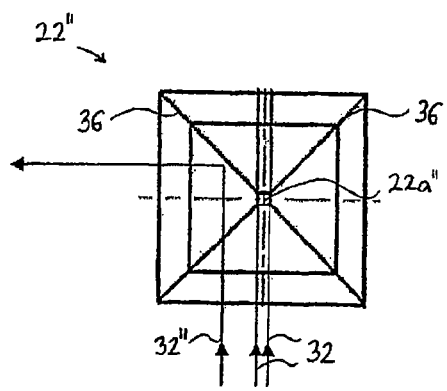
Figure 11B:
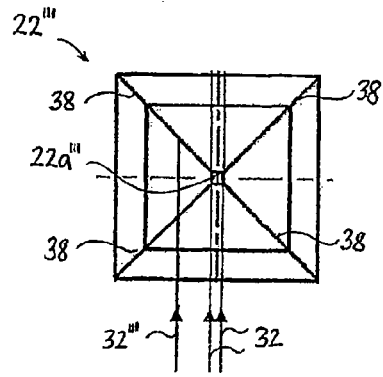

FIG. 4B is a longitudinal sectional view of the light incoupling end of the light collecting optical fiber bundle shown in FIG. 4A, the enlarged portions of which illustrate how the angles formed by the entry surfaces of the elementary optical fibers making up the bundle with the geometrical axis of said elementary fibers change when progressing from the centerline of said optical fiber bundle radially outwards;

FIG. 5A is a longitudinal sectional view of a light collecting optical fiber bundle built up of three offtake bundles;

FIG. 5B is a front view of an embodiment of the optical fiber bundle illustrated in FIG. 5A having a central offtake bundle of an elliptic shape for collecting and directing away laser light incident directly (i.e. without being scattered) upon said bundle;

FIG. 5C is a front view of an embodiment of the optical fiber bundle illustrated in FIG. 5A equipped with a masking plate for the exclusion of laser light incident directly (i.e. without being scattered) upon said bundle;

FIG. 6A is a perspective view of a beam moving device formed with a pair of small angle prisms and used in the optical unit of the flow cytometer according to the invention;

FIG. 6B is a perspective view of another embodiment of the beam moving device, wherein said beam moving device is embodied by the laser source holder itself;

FIGS. 7A and 7B are perspective views of a clamping element having straight walls in a mixer unit of the hydro-pneumatic unit shown in FIG. 1 and a microreactor formed by a conduit portion with a resilient wall, respectively, said conduit portion being arranged within said clamping element and compressed (deformed) thereby in directions perpendicular to one another;

FIGS. 7C and 7D are perspective views of a clamping element having curved walls in a mixer unit of the hydro-pneumatic unit shown in FIG. 1 and a microreactor formed by a conduit portion with a resilient wall, respectively, said conduit portion being arranged within said clamping element and compressed (deformed) thereby in directions perpendicular to one another;

FIG. 8 is a perspective view of a mixer unit of the hydro-pneumatic unit illustrated in FIG. 2, said mixer unit having three reagent branches and being assembled from the clamping elements shown in FIGS. 7A and/or 7B;

FIG. 9 illustrates an automatic positioning process of the illuminating laser light onto the sample in case of an elliptic spot of said laser light;

FIGS. 10A and 10B are a longitudinal sectional view taken along the flow passage and a plan view, respectively, of a preferred embodiment of the flow cell used in the optical flow cytometer according to the invention;

FIGS. 11A and 11B are plan views of further embodiments of the flow cell used in the optical flow cytometer according to the invention.

FIG. 1 illustrates a preferred embodiment of an optical flow cytometer 10 according to the invention that serves for a simultaneous and in vitro measurement of several properties (size, internal granularity, etc.) of a biological sample, for example of formed elements or further cellular components in human or animal whole blood mixed up with one or more reagents chosen from a broad range of reagents. Said cytometer 10 basically comprises three major components that are co-operating with one another: a hydro-pneumatic unit 12 for preparing a solution of the biological sample mixed up with proper reagents and transporting (advancing) it to the location of assay; an optical unit 14 for providing an appropriate illumination of the sample solution during measurement, as well as for collecting and directing the light that is scattered by said sample and carries information associated with the properties of the formed elements of the sample to the sensing element(s); and a controlling and evaluating unit 16 that processes the electrical signals of said sensing element(s) generated by the incident light directed to said sensing element(s) and uses at least a part of the thus obtained pieces of information to control the operation of the optical unit 14 and/or to determine desired properties of the formed elements.

The optical unit 14 comprises a transmitter module 18 providing the illumination needed for the measurement to be performed, a beam moving device 20, a flow cell 22 and an optical fiber bundle 24, all arranged in a light path. The transmitter module 18 comprises a laser source 26 (as illumination device), a driving circuit 27 to provide electric supply of said laser source 26, as well as a temperature stabilizing means 28 (preferably a Peltier element for cooling and a resistive heater for heating; neither is shown in the FIGS.) for stabilizing the temperature of said laser source 26 based on a signal generated by a temperature sensor 29. The laser source provides an illuminating laser light at one or more wavelengths and with a constant averaged light output. Said laser source 26 is preferably formed by one or more laser diodes emitting at different wavelengths, wherein said diode(s) is(are) arranged at a starting point of said light path. An optical axis of the optical unit 14 is specified by a straight line that extends from the laser source 25 to a common end 42 of said optical fiber bundle 24. In said light path, in the propagation direction of the laser light emitted by the laser source 26 there is provided a collimator means 30 forming part of the transmitter module 18 and embodied by one or more suitable optical elements. Said collimator means 30 collimates the laser light. To focus the collimated laser light onto the flow cell 22, a focusing means 31 (in the form of preferably one or more lenses) is arranged in the light path after the collimator means 30. The thus obtained laser beam 32 forms a spot of an elliptic shape within a plane perpendicular to its propagation direction that illuminates the flow cell 22 in a pre-defined zone thereof. The power density distribution of said laser beam 32 at the centerline of the flow cell 22 in a plane perpendicular to the light path is a Gaussian distribution (from now on Gaussian). To shape the collimated and focused laser beam 32, slots 33 of given width and extending at right angles to one another can be used that are optionally arranged in the light path after said focusing means 31. The function of said slots 31 is to cut off the external portions of the Gaussian laser beam 32 which are of smaller power densities and thereby to decrease the amount of light used for the illumination and to eliminate the light that is reflected to the laser source 26 from various parts of the optical unit 14 as much as possible. It should be noted that, as it will be discussed later in relation to FIGS. 10 and 11, a flow cell with a particular design can also play the role of said slots 33.

In an embodiment of the cytometer shown in FIG. 1 the laser beam 32 exiting the transmitter module 18 falls on an automated beam moving device 20 arranged in the light path. Said beam moving device 20 ensures that the flow cell 22 be illuminated just in the prescribed zone (beam positioning). In one embodiment (see FIG. 6A), said beam moving device 20 is formed by a pair of small angle prisms 34a, 34b, wherein said prisms 34a, 34b are antiparallel to each another in the normal position. As a result of this, the outgoing and the incoming laser beams 32 are parallel to each other as far as their axes are concerned. The prisms 34a, 34b can be rotated together and/or independently of one another around a common geometrical axis that basically coincides with the optical axis and thereby the size of the spot of the illuminating laser beam 32 can be modified. Through a full 360°-rotation of the pair of prisms, the illuminating spot of the laser beam 32, depending on the alignment of said pair of prisms, sweeps over an circular ring shaped region lying in a plane perpendicular to the optical axis. Inner diameter d of said ring shaped region depends on the distance between the prisms 34a and 34b and their apex angle. Outer diameter D of said ring shaped region is determined by the maximum deflection angle of the laser beam 32 relative to the optical axis, which is equal to the double of the refracting angle of said small angle prisms 34a, 34b. When the laser beam 32 passes through said pair of prisms, it is repeatedly refracted in a direction that depends on the angle positions of the prisms and, hence, its propagation direction can be modified, according to needs. Consequently, after leaving the beam moving device 20, the laser beam 32 propagates in a direction that is defined by the flow cell 22 and the optical fiber bundle 24.

In a possible further embodiment, said beam moving device 20 is formed by the holder of the laser source 26 itself (see FIG. 6B). In this case, the required propagation direction of the laser beam 32, that is the propagation direction defined by the flow cell 22 and the optical fiber bundle 24 is set by said holder by tilting the laser source 26 from a plane perpendicular to the optical axis in a given angle into the propagation direction of the laser beam 26. Here, the maximum displacement of the laser beam 32 and thus a region 35' that can be swept by the illuminating spot are defined by the maximum tilting angle of the moving mechanism.

The laser beam 32 leaving the beam moving device 20 falls on the flow cell 22 of the optical unit 14. In its simplest possible embodiment, a cylindrical or prism-shaped oblong body forms the flow cell 22 (see e.g. FIGS. 1, 2 and 4A), wherein a flow passage 22a with a longitudinal extension is formed within the bulk of said body. Consequently, said body exhibits a given wall thickness along the propagation direction of the laser beam 32. In general, the cross section of the flow passage 22a taken in a plane perpendicular to the length of the flow cell 22 is preferably circular or rectangular in shape. The diameter of the flow passage 22a ranges from at least 100 µm to at most several hundreds µm, it is preferably about 250 µm in size. As it was mentioned earlier, the laser beam 32 illuminates the flow cell 22 at the centerline of its passage 22a in a basically elliptical spot (the illumination zone) with a Gaussian power density distribution. The lengths of the minor and the major axes of said elliptical spot fall between about 30 µm to about 50 µm and between about 150 µm to 300 µm respectively. Preferably, said lengths are about 30 µm and about 200 µm, respectively, in size. The flow cell 22 is arranged within the optical unit 14 so as to contain the flow passage 22a in a position basically perpendicular to the optical axis. Accordingly, the sample to be assayed flows within the flow cell 22 in a direction essentially at right angle to the optical axis of the optical unit 14.

Possible further embodiments 22', 22", 22'" of the flow cell, that can equally be used in the cytometer 10 according to the invention, are presented in FIGS. 10A and 10B and in FIGS. 11A and 11B. Each of said flow cells 22', 22", 22'" are made of four, preferably congruent, prisms of truncated pyramid in shape with rectangular base and top surfaces in such a manner that the walls of the flow passages 22a', 22a", 22a'" are defined by the top surfaces of the prisms of truncated pyramids in a position where said prisms are faced to each other with the top surfaces and joined together (e.g. by means of bonding) in pairs along the respective side surfaces. Due to this design, in the above embodiments of the flow cells 22', 22", 22'", said passages 22a', 22a", 22a'" exhibit shrinking entrance regions and extending exit regions. The prisms forming the flow cells 22', 22", 22'" are made of glass, quartz, or plastic materials, as well as of any suitable materials that are transparent at the wavelength(s) of laser light(s) emitted by the laser source 26 and unaffected by the substances directed through said passages 22a', 22a", 22a'''; choosing an appropriate material is obvious to a skilled person in the art.

Each flow cell 22', 22", 22''' is constructed in a manner so as to hinder the propagation of an incident illuminating laser light towards the optical fiber bundle 24 in regions located outside of the passages 22', 22", 22'''. Therefore, the amount of illumination reaching said optical fiber bundle 24 directly decreases significantly which facilitates performing measurements and improves the signal-to-noise ratio. As can be seen in FIG. 10B, for the flow cell 22' this is achieved by preparing the pairs of prisms located opposite to each other from materials of different refractive indices in pairs, wherein the materials and the refractive indices of the prisms are chosen so as to deflect a laser beam 32' reaching said flow cell 22' in regions located outside of the passage 22a' from its original direction of propagation to a significant extent (preferably by at least 45°) by the refraction(s) taking place at the contacting side surfaces, as interfaces, of the prisms forming the flow cell 22' when said laser beam 32' passes said flow cell 22'. Materials of the prisms are preferentially chosen in such a way that, the laser beam 32' suffer a total internal reflection at the last interface in its propagation direction when passing through the flow cell 22'.

As it is shown in FIG. 11A, the above discussed desired behaviour of a further embodiment of the flow cell 22" is achieved by constructing in the propagation path of laser beam 32" passing through the flow cell 22" in regions located outside of the passage 22a" a reflecting surface 36, preferentially in the form of a metallic thin film, at the last interface of the prisms joined to constitute the cell. Said reflecting surface 36 deflects the incident laser beam 32" to a significant extent from its original direction of propagation and thus it cannot reach the bundle 24 of the optical fibers.

As it is shown in FIG. 11B, the above discussed desired behaviour of a further embodiment of the flow cell 22''' is achieved by arranging in the propagation path of laser beam 32''' passing through the flow cell 22''' in regions located outside of the passage 22a''' an attenuation layer 38, preferentially in the form of a coating made of material(s) optically absorbing at the wavelength(s) emitted by the laser source 26, at least in a portion of the interfaces of the prisms joined to constitute the cell. Said attenuation layer 38 absorbs a part, ideally a whole amount of the energy of the incident laser beam 32''' and thus only a small amount of light reaches directly the bundle 24 of the optical fibers through the material of the flow cell 22'''.

Returning now to FIGS. 1 and 4A, during the measurement the sample to be assayed flows through the passage 22a of the flow cell 22, wherein the objects 40 of the assay (depending on the sample, for example formed elements of whole blood or other cellular components and similar elements) travel essentially in the centerline of the sample flow one by one, as will be discussed later in detail. During travelling, the objects 40 reach a region of the passage 22a that is illuminated by the laser beam 32 (that is, the illumination zone), where a part of the laser light striking said objects 40 scatters to all directions of space according to a given distribution (i.e. in a given pattern). As is well-known, the objects 40 differing in size and shape and also having optionally an internal structure scatter the striking light to various extent into the different spatial regions. From the analysis of the scattered light with respect to the spatial pattern, for example by given conical angle ranges, a conclusion can be drawn with regard to the sought properties of said objects 40.

To this end, as a next step of the measurement there is a need for collecting the laser light scattered into the various spatial regions. This is the task of the optical fiber bundle 24 that has a (common) frontal end 42 with a particular shape. Depending on the number of different spatial regions selected for a study of the objects 40 (consisting of e.g. the cellular components), the optical fiber bundle 24 is split into a plurality of separate offtake bundles 24-1, 24-2, . . . , 24-p, wherein every single offtake bundle 24-1, 24-2, . . . , 24-p transmits laser light scattered into a certain spatial region under study and collected therefrom to the controlling and evaluating unit 16, the components of which will be discussed later.

As it is shown in FIGS. 4A, 4B and 5A to 5C, said optical fiber bundle 24 is built up of per se known elementary optical fibers 44 made of glass or a plastic material, wherein the diameters of each optical fiber 44 ranges from about 70 μm to about 500 μm. The elementary optical fibers 44 are located closely to each other, accordant to the most compact space filling scheme and are coupled to each other by bonding or sintering. Consequently, the geometrical losses among the optical fibers 44 are minimal. The frontal end 42 of the optical fiber bundle 24 is divided into (preferentially ring-shaped) regions by means of separating plates 45. Optical fibers 44 belonging to the respective regions form the offtake bundles 24-1, 24-2, . . . , 24-p (FIG. 1) that are connected to said controlling and evaluating unit 16. The optical fiber bundle 24 is equipped with an elongated masking plate extending perpendicular to the optical axis on its frontal end 42 (FIG. 5C). In a possible further embodiment, the optical fiber bundle 24 comprises a central offtake bundle 47 of elliptical shape (FIG. 5B) instead of said masking plate 46. The task of the masking plate 46 and the elliptical-shaped bundle 47 is to obstruct the path of illuminating light reaching directly (that is, without being scattered) said frontal end 42 by excluding and receiving/leading away, respectively, of said light. It should be here noted, that the masking plate 46 can also be replaced by a coating applied onto a surface of the flow cell 22 facing said optical fiber bundle 24 in an appropriate pattern if the light absorbent material described in connection with FIG. 11B is made use of as the material of the coating.

In particular, FIG. 5A illustrates an embodiment of the optical fiber bundle 24, wherein said separating plates 45 divide the optical fibers 44 into three respective concentrical regions, that is a central region that receives the laser light incident directly upon the optical fiber bundle 24, as well as a so-called low-angle region and a so-called high-angle region accordingly as from which spatial region they collect the incoming laser light. This particular embodiment of the optical fiber bundle 24 can be used preferentially in a cytometer that aims at analysing formed elements in a sample of human or animal whole blood.

Returning now to FIG. 4B, the object 40 to be analysed travels through the illuminating laser beam 32 having an elliptical-shaped spot and a Gaussian power density. The intensity of the light scattered by the object 40 depends on the structure of said object 40 and the intensity of the illuminating light which is the highest on the centerline of the Gaussian laser beam 32. A direct light 32a arising from the illuminating laser light 32 and a scattered light 32b scattered by an object 40 travelling through the centerline of the Gaussian beam strike a certain optical fiber 44 at different angles ($\phi_2$ and $\phi_1$, respectively), and hence depending on the angle of incidence, the efficiencies of the coupling into the optical fiber will also differ.

An elementary optical fiber 44 located at the centerline of the optical fiber bundle 24 has got an entry surface 50 perpendicular to the optical axis; the incoupling coefficient is the largest for a beam that strikes an optical fiber 44 located at the center in parallel. In case of an entry surface 50' forming an angle α with the longitudinal axis of the optical fiber 44, the direction associated with the largest incoupling coefficient swivels by an angle of $\phi_1$, when going away from the centerline of the optical fiber bundle 24. Going away from the ideal direction of incoupling, the incoupling coefficient for an incident beam decreases and when a certain limiting angle is exceeded, said incident beam can no longer couple into the optical fiber 44 and is absorbed by the material situated among the fibers. Due to the design of the common end 42 of the optical fiber bundle 24 according to the invention, the incoupling characteristics of the elementary optical fibers 44 is modified so as to have the maximum value in a direction of apparent objects 40 to be analysed. The incoupling efficiency will be maximal for the whole optical fiber bundle 24 with no making use of an additional condenser lens. Focal point of the direct illuminating laser light differ from the apparent focal point of the scattered light, and hence the incoupling coefficient associated with it will be smaller for each elementary optical fiber 44 than the incoupling coefficient associated with the scattered light.

In light of the above, the common end 42 of the optical fiber bundle 24 can be prepared as a plate perpendicular to the optical axis or as a hemisphere or as an aspherical surface that can be fabricated by optical production plant known by a skilled person in the art, preferably by means of grinding.

In a preferred embodiment, the common end 42 of the optical fiber bundle 24 is formed as a hemisphere with a radius equal to about half of the distance between an apparent object 40 to be assayed and the optical fiber bundle 24.

Through the desired design of the common end 42 of the optical fiber bundle 24 it can be achieved without using a condensor lens that the laser light scattered by the object 40 to be assayed couples into the elementary optical fibers 44 with the highest efficiency. The illuminating light coming from a direction differing from this couples into the optical fibers 44 with lower efficiencies. By the appropriate design of the common end 42 of the optical fiber bundle 24, the useful scattered light power appearing on the input of an analogue amplifier module 52 increases. Moreover, the illuminating light power, and in turn the noise generated thereby, appearing on the input of said analogue amplifier module 52 decreases. That is, the signal-to-noise ratio improves when a cytometer 10 according to the invention is used with the optical fiber bundle 24 having a common end 42 formed as discussed previously.

Returning now to FIG. 1, the laser light collected from spatial regions to spatial regions and transmitted by said optical fiber bundle 24 is received by the controlling and evaluating unit 16, more precisely its analogue amplifier module 52 which is a multichannel amplifier. On its input, said amplifier module 52 comprises sensing elements or detectors $A_1, \ldots, A_p$ (preferably PIN type or an avalanche photodiodes; not shown in the FIGS.), one for each channel, that are connected to transimpedance amplifiers. Each channel comprises more than one AC-coupled stage for amplifying further, level matching and filtering the electrical signal obtained. An electrical signal proportional to the incident light power appears on the output of the analogue amplifier module 52. In a further embodiment, a further electrical signal proportional to the average incident light power also appears on the output of said analogue amplifier module 52.

The analogue amplifier module 52 is connected to an analogue-to-digital converter module 53 of said controlling and evaluating unit 16, which digitizes the output signals of the analogue amplifier module 52 channel by channel and transmits them to a signal processing unit 54.

The signal processing unit 54 determines the parameters of the digitized electric pulses, for example their peak values, lengths in time, average values, integrals, signal shapes, that correspond to the light scattered by said objects 40 and are generated on the output of the analogue amplifier module 52 and then are digitized by the analogue-to-digital converter module 53. Then, an evaluation unit 55 of the controlling and evaluating unit 16 derives from these parameters the physical properties of the objects 40 in the sample. According to needs, the thus obtained physical properties can be displayed and/or stored for a later usage in an appropriate storage medium.

To control/position the illuminating laser beam 32, based on a part of the parameters determined by said signal processing unit 54, a control unit 56 governs the beam moving device 20 by means of a motor 58 through a motor driving means 57 and an appropriate transmission, as will be discussed later in detail.

It should be here noted that in a preferred embodiment of said controlling and evaluating unit 16 the analogue-to-digital converter module 53, the signal processing unit 54, the evaluation unit 55 and the control unit 56 (or one or more thereof) can be replaced by a properly programmed computer that provides for digitizing the analogous electrical signals, evaluating the digitized signals, as well as displaying (preferably in the form of e.g. scatter plots illustrating the populations of the formed elements in the sample separately) and storing, if needed, the thus obtained results and adjusting the illuminating laser beam 32 based on said results, be it either desired or required.

As it is shown schematically in FIG. 5A, the ends of the offtake bundles 24-1, ..., 24-$p$ of the optical fiber bundle 24 are also of particular design. The burden of said design is that in case of detectors with sensing areas smaller than the cross-sections of the bundles 24-1, ..., 24-$p$, light leaving the outcoupling ends of said bundles 24-1, ..., 24-$p$ reach the sensing areas of sensing elements $A_1, \ldots, A_p$ in a proportion as high as possible without making use of condenser lenses. To this end, the outcoupling ends of the bundles 24-1, ..., 24-$p$ are formed so as to specify a spherical or an aspherical surface. In such a case, in order that the light exiting from each of the bundles 24-1, ..., 24-$p$ and forming a convergent beam strike sensing areas of the sensing elements $A_1, \ldots, A_p$ in full amount, said sensing elements $A_1, \ldots, A_p$ must be arranged at a certain distance apart from the ends of the bundles 24-1, ..., 24-$p$. In this way, an irradiation with no geometrical losses of the sensing areas of detectors can be accomplished without a use of additional optical elements (e.g. lenses). In a possible further embodiment, wherein the sensing areas of detectors are larger than the cross-sections of the offtake bundles 24-1, ..., 24-$p$, the outcoupling ends of said bundles 24-1, ..., 24-$p$, which are coupled to the sensing elements $A_1, \ldots, A_p$, of the optical fiber bundle 24 are each formed as a plane perpendicular to the optical axis of the bundle 24-1, ..., 24-$p$ at issue.

In what follows, the hydro-pneumatic unit 12 of the flow cytometer 10 according to the invention and its operation is discussed in detail with reference to FIGS. 1 and 2.

The task of the hydro-pneumatic unit 12 of the cytometer 10 according to the invention is to produce the sample solution of a sample to be analysed that is suitable for being assayed in an optical type of analysis, to prepare the thus obtained sample solution for the analysis and then to feed it into the flow passage 22$a$ of the flow cell 22 at a constant volume rate, as well as to advance it through said passage 22$a$ during the measurement. Said production and preparation of the sample solution comprises mixing the sample to be assayed with the various reagents, as well as controlling temporal and spatial course of the (bio)chemical reactions taking place within the mixture (in particular, adjusting the volume ratios of the reagents to be mixed up, the incubation times and the temperature)—all that is performed in a biochemical preparation unit 64. Feeding the prepared sample solution into the flow cell 22 takes place through a per se known special unifying member 66 that provides simultaneously for a hydrodinamical focusing of said sample solution as well. Hydrodinamical focusing performed through the application of a sheath liquid of suitable parameters (temperature, viscosity, etc.) is per se known, too.

The hydro-pneumatic unit 12 comprises a closed liquid flow path extending between a starting point and an end point. Said liquid flow path consists of a sample branch 62 and a sheath liquid branch 63 that preferentially extend parallel to one another in the embodiment disclosed. The starting point of the sample branch 62 and of the sheath liquid branch 63 is a tank 60 kept at a certain (preferably atmospheric) pressure for storing the sheath liquid. To the sample branch 61, in different locations thereof, containers 60-1, ..., 60-*n* are connected through valves $V_1, \ldots, V_n$, respectively, that serve for the storage of the reagents—also included the sample itself. For feeding the reagents from the containers 60-1, ..., 60-*n* into the sample branch 62, reagent pumps 69-1, ..., 69-*n* in fluid communications with an inlet of the respective valve $V_1, \ldots, V_n$ are provided. The sample branch 62 and the sheath liquid branch 63 meet in the unifying member 66, from here they run together through the passage 22*a* to the end point. At the end point of the hydro-pneumatical unit 12, a vacuum tank 59 at a pressure lower than the pressure maintained in said tank 60 by about 0.35 to 070 bar is arranged, said tank 60 is for receiving and optionally also for collecting the sample solution leaving the flow cell 22. Said liquid flow path between the starting point and the end point is provided by conduits that branches away, according to needs. The biochemical preparation unit 64, the unifying member 66 and the flow cell 22 are inserted into said conduits one after the other (in the given order) in a flow direction that points from the starting point to the end point. Moreover, upstream said unifying member 66, in flow direction immediately before it, two-way cross valves $V_m$ and $V_t$, and a valve $V_s$ are inserted into the sample branch 62 and into the sheath liquid branch 63, respectively. The sample flow exiting from the flow cell 22 reaches the vacuum tank 59 via a valve $V_v$. One of the inlets of the cross valve $V_m$ is in fluid communication with the preparation unit 64, while the remaining inlet thereof is connected into the sheath liquid branch 63 upstream the valve $V_s$. The outlet of the cross valve $V_m$ is in fluid communication with the inlet of the cross valve $V_t$. One of the outlets of the cross valve $V_t$ opens into the unifying member 66, while the remaining outlet thereof is connected into the flow path through a bypass 65 in flow direction between the flow cell 22 and the valve V. Said cross valves $V_m$, $V_t$ and the valves $V_s$, $V_v$ are preferably precision valves that influence the flow conditions prevailing within the hydro-pneumatical unit 12, 12'.

Figure 3:
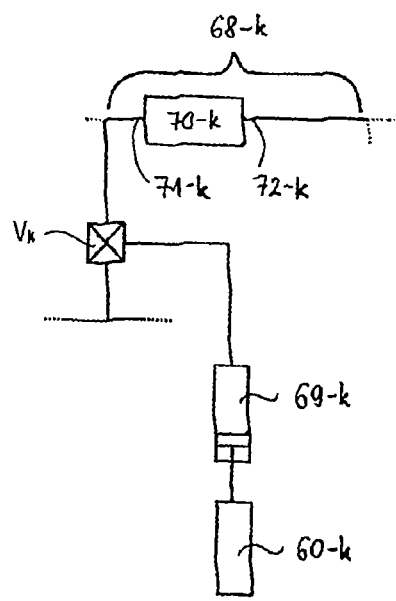
FIG. 3 is a block diagram of the k-th member of the biochemical preparation unit of the hydro-pneumatic unit shown in FIG. 1.

For treating/blending in various reagents, the biochemical preparation unit 64 is of a modular construction: it comprises any number of reagent branches 68-1, ..., 68-*n* with reagents connected to one another (in the embodiment illustrated in FIG. 1, the number of reagent branches is n). Said reagent branches 68-1, ..., 68-*n* are preferentially of basically identical structure, however, this is not a need. FIG. 3 shows schematically the k-th reagent branch 68-*k*. Said k-th reagent branch 68-*k* comprises a container 60-*k* for storing the k-th reagent, a reagent pump 69-*k* capable of supplying the reagent concerned at a preset feeding rate, a two-way valve $V_k$ allowing feeding-in of the reagent, as well as a microreactor 70-*k* with an inlet 71-*k* and an outlet 72-*k*. The valve $V_k$ formed as a cross valve and provided by a preferentially electronically regulated magnetic valve—accordant to the actual flow path specified by it—leads the k-th reagent supplied by the reagent pump 69-*k* or the sheath liquid to the inlet 71-*k*. The inlet of a microreactor within a selected interim (e.g. the k-th) reagent branch of the modular biochemical preparation unit 64 is in fluid communication with the outlet of the microreactor within the preceding (i.e. the (k−l)-th) reagent branch in flow direction, while the outlet of the microreactor of said interim selected reagent branch is in fluid communication with the inlet of the microreactor within the subsequent (i.e. the (k+l)-th) reagent branch in flow direction through suitable connection elements 61, as is shown in FIG. 1. In said preparation unit 64, the inlet of the very first reagent branch 68-*n* in flow direction and the outlet of the very last reagent branch 68-1 in flow direction are connected to the container 60-*n* and to the unifying member 66, respectively, via said respective cross valves $V_m$ and $V_t$. The sample to be analysed is preferably arranged in the container 60-*n* of the very first reagent branch 68-*n*, however, this is not compulsory. At least one of said reagent branches may optionally comprise calibration substance(s) to be used for the automated beam positioning that will be discussed later in detail. The respective reaction time in each microreactor 70-1, ..., 70-*k* is directly proportional to the volume of the microreactor concerned and is inversely proportional to the liquid flow flowing through the microreactor concerned.

FIG. 2 is a block diagram of a hydro-pneumatical unit 12' to be used in the cytometer 10 according to the present invention, that is equipped with a biochemical preparation unit 64' comprising three reagent branches 68-1, 68-2, 68-3. This embodiment is preferentially for the analysis of formed elements in human or animal whole blood. Here, the reagent branch 68-1 contains the sample of whole blood (optionally blended with an isotonic diluent), addition of a hemolysing agent initiating the hemolysis takes place within the reagent branch 68-2, while supply of a stabilizing agent, i.e. of a reagent that stops the hemolysis, is performed in reagent branch 68-3.

A major task of the biochemical preparation unit 64, 64' is that the exiting sample flow be as homogeneous as is possible in its whole volume and the desired reactions take place to the extent as high as possible, that is, the requested biochemical preparation of the sample flow take place. The addition of reagents into the sample flow takes place through the operation of consecutive reagent branches (simultaneously or one after the other) by means of setting respective valves.

The blend of the sample flow and the reagents added to it must be subjected to homogenization. To this end, each microreactor is equipped with a mixer unit. Such a mixer unit 80 is illustrated schematically in FIG. 8. The mixer unit 80 squeezes the external resilient wall of the microreactor and forms thereby chambers and channels of various shapes within the internal room of said microreactor without actually breaking it. Said mixer unit 80 is also modular in construction: it is formed by means of combining a required number of elementary clamping elements. The elementary clamping elements 82, 82' and the microreactors provided by the deformed conduits 83, 83' obtained through the application of said clamping elements 82, 82' are illustrated in FIGS. 7A, 7C and FIGS. 7B, 7D, respectively. Said clamping elements 82, 82' are formed by at least two walls 85*a*, 85*b* and 85*a'*, 85*b'* arranged a given distance apart and extending between planar bases 84, 84' perpendicular to said bases 84, 84', said bases 84, 84' are arranged a given distance apart, wherein each wall 85*a*, 85*b* and 85*a'*, 85*b'* is provided with a slot 86*a*, 86*b* and 86*a'*, 86*b'*, respectively, that receives the microreactor 83, 83'. The slots 86*a*, 86*b* extend essentially perpendicular to one another. Similarly, the slots 86a', 86b' also extend essentially perpendicular to one another. Said slots 86a, 86b and 86a', 86b' can be of any shape; they can be limited by straight edges (see FIG. 7A) and/or a part of the limiting edges can be arcuate (see FIG. 7C) as well. The shapes of the channels and the chambers are determined by the shapes of the clamping elements 82, 82', the dimensions of said slots and the resilience of the wall of the microreactor 83, 83'. The emerging chambers and channels induce a turbulent flow of the mixture flowing therethrough, thus they perfectly mix up the components of said mixture. The extent of mixing—besides the shapes of the chambers and the channels—can also be influenced by the number of clamping elements 82, 82' actually applied. The clamping elements 82, 82' can be formed in a flawless and simple manner, for example by means of injection moulding or extrusion of a plastic material, or by casting of a metal. Furthermore, due to the modular structure, the mixer unit 80 prepared by means of said clamping elements 82, 82' can easily be repaired in case of being damaged (through e.g. replacing the damaged clamping elements) or can be simply modified when a restructuring is needed. Similarly, the damaged or even clogged sections of the microreactor 83, 83' can also be simply repaired/replaced.

Performing reactions of the reagents and the sample solution with an optimal result requires, in general, a narrow temperature range. To this end, in order to keep the temperature within a preset range, the reagent branches 68-1, ..., 68-n of the biochemical preparation unit 64 are subjected to tempering by means of a temperature regulator 88. Said temperature regulator 88 achieves an increase in temperature by suitable heating means, while it achieves a decrease in temperature by suitable cooling means, preferably by means of thermoelectric (Peltier) means.

To perform a measurement, all three major components of the cytometer 10 according to the invention are activated. In particular, the hydro-pneumatical unit 12 prepares to produce a sample flow apt for being measured and to deliver it into the flow cell 22, the optical unit 14 generates the laser beam 32 required for the desired irradiation of the flow cell 22, while the controlling and evaluating unit 16, in case of need, provides for an appropriate adjustment/positioning of the illuminating spot of the laser beam 32, as will be discussed later in more detail.

Before commencing the measurement, the reagent branches 68-1, ..., 68-n and the sample branch 62 are filled up with reagents (e.g. also with the sample arranged in the container 60-n) by means of the reagent pumps 69-1, ..., 69-n from the containers 60-1, ..., 60-n at the following positions of the valves: the valves $V_1, ..., V_n$ and the cross valve $V_m$ conduct (i.e. open) towards the unifying member 66, the cross valve $V_t$ conducts (i.e. open) towards the by-pass 65, as well as the valve $V_s$ is in the closed position and the valve $V_v$ is in the open position.

After completing the above filling up, reagent supplies of the reagent branches 68-1, ..., 68-n are stopped by changing over the valves $V_1, ..., V_t$, and, at the same time, to fill up the reagent branches 68-1, ..., 68-n with a sheath liquid, said reagent branches 68-1, ..., 68-n are connected with the tank 60 storing said sheath liquid. Due to the difference between the pressure prevailing within the vacuum tank 59 and the pressure prevailing in the tank 60 storing the sheath liquid, a flow is induced through the cross valve $V_t$. Due to the flow in the sample branch 62, the sample solution and the reagents fed into the sample branch 62 from the respective reagent branches 68-1, ..., 68-n through the connecting elements 61 mix up and react with each other as they advance within the microreactors 70-1, ..., 70-n provided with mixer units 80.

Then the cross valve $V_t$ arranged in the sample branch 62 is changed over a position in which it conducts towards the unifying member 66, and due to the already mentioned pressure difference, the sample solution will travel towards the vacuum tank 59 through the unifying member 66. In order to deliver (that is, to feed) the prepared sample flow to the unifying member 66 relatively rapidly, it is preferred to keep the valve $V_s$ within the sheath liquid branch 63 temporarily in its closed position. In this way, the difference between the pressures prevailing within the vacuum tank 59 and the tank 60 fully arises in the sample branch 62 which results in the acceleration of said feeding of the sample solution. When the valve $V_s$ is opened, due to the pressure difference concerned a flow of sheath liquid commences in the sheath liquid branch 63 towards the vacuum tank 59 through the unifying member 66 and the flow cell 22.

A mixing ratio of the sample solution and a selected reagent, which is e.g. fed at the k-th connection element, is influenced by the ratio of the flow impedance (from now on: impedance) of that part of the liquid flow path which extends from the tank 60 to the k-th connection element 61 to the impedance of the whole k-th reagent branch. The reaction time depends on the impedance ratios relevant for the entire liquid flow path. Impedancies of the reagent branches 68-1, ..., 68-n each can be set, for example, by adjusting the compressing forces exerted by the clamping elements 82, 82' forming the mixer unit 80 onto the wall of the microreactor 83, 83' in each branch, wherein regulating the compressing forces can take place either manually or in an automated manner.

The thus prepared sample solution that was mixed up with reagents and went through the appropriate (bio)chemical reactions flows into the unifying member 66. Due to its geometrical construction, said unifying member 66 places the sample solution coming from the sample branch 62 into the centerline of the sheath liquid flow coming from the sheath liquid branch 63 and constricts its cross-sectional size to a cross-section that is smaller than the cross-section of the passage 22a of the flow cell 22. The thus obtained composite stream, i.e. the sample surrounded by the sheath liquid flows from the unifying member 66 into the passage 22a of the flow cell 22. Said flow is laminar, and thus the sheath liquid and the sample do not mix up. During travelling through the flow passage 22a, the sheath liquid keeps the sample all the time at the centerline of the passage 22a. To create and maintain the laminar flow, the flow velocities of the sample flow and the sheath liquid flow entering the unifying member 66 should be about identical at the entry point of the sample flow. It is noted that the velocity of the sample solution can be varied a little bit around its optimal value without destroying the laminar flow. An adjustment of the adequate velocities takes place by the flow impedancies of the sample branch 62 and the sheath liquid branch 63 without making use of the reagent pumps 69-1, ..., 69-n. The ratio of the volume flow rates setting in within the two branches is inversely proportional to the ratio of impedancies of those portions of the entire liquid flow path that form said two branches and uniquely defines the cross-sectional area of the developing sample flow. Consequently, the cross-section area of the sample solution travelling in the flow passage 22a of the cytometer 10 according to the invention can eventually be controlled (to a small extent) by varying the ratio of the flow impedance of the sample branch 62 to the flow impedance of the sheath liquid branch 63. In particular, by increasing the impedance of the sample branch 62 (e.g. by reducing the number of reagent branches) or by decreasing the impedance of the sheath liquid branch 63, the cross-sectional area of the sample flow decreases, and vice versa. As a consequence, the measurement can be performed on a stable sample flow with no fluctuations, which allows to derive more precise results. It is noted that the size of a pressure drop building up along the liquid flow path as a whole can be changed by a valve $V_v$ inserted into between the flow cell 22 and the vacuum tank 59; said valve $V_v$ can be e.g. an electronically governed precision valve of variable flow rate. It is also noted that the ratio of the flow velocity in the sample branch 62 to the flow velocity in the sheath liquid branch 63 can be adjusted in a given range arbitrarily and set to a desired value by means of the valve $V_s$. Hence, formation of the laminar flow of the sample solution and the sheath liquid can be facilitated within the unifying member 66.

At the same time, the laser source 26 emits the illuminating laser light that strikes the flow cell 22 in the form of the laser beam 32 that had gone through a beam shaping governed by the control unit 56 and irradiates the liquid stream flowing in the passage 22a. The sample surrounded by the sheath liquid and prepared biochemically as required and flowing through the flow cell 22 crosses the illuminating laser beam 32. Meanwhile, a portion of light of said laser beam 32 is spatially scattered by the objects 40 of said sample. Depending on the construction of the flow cell 22 used (see the flow cells 22', 22", 22''' discussed with reference to FIGS. 10A, 10B and 11A, 11B), said laser beam 32 is absorbed, deflected from its initial direction or transmitted by the flow cell 22. The scattered light exiting the flow cell 22 in a definite spatial region (here, in accordance with FIG. 2, in a low-angle region that forms an angle with the optical axis falling preferably between about 1.5° and about 3°, and in a high-angle region that forms an angle with the optical axis falling preferably between about 4° and about 8°; further spatial regions can also be defined, if desired) strikes the common end 42 of the optical fiber bundle 24, where it couples into the elementary optical fibers in a manner discussed earlier, said light then reaches via the offtake bundles 24-1, . . . , 24-p sensing surfaces of the sensing elements $A_1, \ldots, A_p$ located on the input of the amplifier module 52 where generates adequate electrical signals. The thus obtained electrical signals are then processed in a manner already discussed.

After the sample flow to be measured has travelled through the passage 22a in its entire length, by changing over the cross valve $V_m$, along with an open position of the valves $V_v$ and $V_s$ and an unaltered position of the cross valve $V_t$, due to the existing pressure difference only sheath liquid will flow through the unifying member 66 and the flow passage 22a that performs a cleaning/flushing of said elements and thus prepares the flow cell 22 for the measurement of the following sample.

It is noted here that when the valves $V_1, \ldots, V_n$, the cross valves $V_m$, $V_t$ and the valves $V_s$, $V_v$ of the cytometer 10 according to the invention are properly adjusted (that is, by their setting into closed/opened positions, as desired), the steps of filling-up, mixing, feeding and measuring can be effected merely by the difference in pressures prevailing within the vacuum tank 59 and the tank 60 storing the sheath liquid, as is clear in view of the previous disclosure for a skilled person in the art. In such a case, the task of the reagent pumps 69-1, . . . , 69-n is limited e.g. to meter required amounts of the proper reagents. The pressure-governed mixing, as well as the measuring and the feeding can take place simultaneously—in this case the cross valve $V_t$ is open towards the unifying member 66 and, hence, the mixture gets directly into the flow cell 22. In such a case, the reaction time is influenced by the impedance of the flow cell 22.

Biochemical preparation and measurement of the sample can be performed in two separate steps, too. The biochemical preparation unit 64, 64' is directly connected to the pressure reservoirs (that is, to the tank 60 storing the sheath liquid and to the vacuum tank 59) through the cross valves $V_t$, $V_m$. Due to the pressure difference between the tank 60 and the vacuum tank 59, mixing of the reagents and the sample takes place as discussed earlier, however, the prepared sample does not flow immediately through the flow cell 22. Instead, it travels through the flow cell 22 in a separate step after the cross valve $V_t$ has been switched over—here, the biochemical preparation unit 64, 64' can be disconnected from the sample branch 62 by means of the cross valve $V_m$. In this case, the flow impedance of the sample branch 62 and the flow impedance of the sheath liquid branch 63 that govern the laminar flow can be adjusted separately in an optimal manner in the two steps.

In a preferred further embodiment of the invention, said biochemical preparation takes place not in accordance with the pressure-governed way discussed above, but it is forced by the reagent pumps 69-1, . . . , 69-n. In this case, valves $V_1, \ldots, V_n$ connect the reagent branches 68-1, . . . , 68-n to the reagent pumps 69-1, . . . , 69-n and respective volume rates are created by said reagent pumps 69-1, . . . , 69-n. Such an arrangement is preferred when numerous reagents are present, as respective reaction parameters can be adjusted more easily thereby.

As it was referred to earlier, for an accurate measurement, positioning of the illuminating laser beam 32 onto the flow cell 22, or rather onto the objects 40 travelling in the passage 22a, i.e. adjusting the cytometer 10, is absolutely necessary. In what follows, an automated positioning of the laser beam 32 of the cytometer 10 according to the invention will be discussed with reference to FIG. 9. The aim of said automated positioning is to adjust the illumination spot 32' of the elliptical laser beam 32 with a Gaussian power density distribution optimally, whereby irradiation of each object of a sample flow that flows through the optical cell 22 is the most uniform possible. With this, our object on the one hand is to decrease the noise emerging due to the unevenness of illumination, and on the other hand to provide such a tool by means of which adequacy of the laser beam 32 and the optical elements used can easily be checked even during a continuous operation of said cytometer 10.

Automated positioning of the laser beam 32 takes place in two separate steps: in a coarse- and an in a fine-positioning step. In the coarse-positioning step, there is no liquid flowing in the passage 22a. In the fine-positioning step, a liquid is flowing through the passage 22a, in its centerline, just as takes place in the case of the sample flow, wherein said liquid is a liquid substance comprising calibration objects (e.g. microballs) of the same size or a sample derived from whole blood. Said calibration objects can be stored optionally by one of the reagent branches not used for other purposes and/or they can be introduced into the flow cell 22 from the outside.

To perform the automated positioning, a particular design of the optical fiber bundle 24 extending along the optical axis of the optical unit 14 is exploited. In particular, as is shown in FIGS. 5B and 5C, said optical fiber bundle 24 is formed with an elliptical-shaped central offtake bundle 47 or a centrally located masking plate 46. With reference now to FIG. 9, such a positioning method is outlined, wherein the optical fiber bundle 24 comprises an elliptical-shaped central offtake bundle 47. In such a case, the electrical signal (in particular, e.g. the electrical voltage U) proportional to the mean light power and generated in the output channel of the amplifier module 52 that is associated with the bundle 47 will be at its maximum value when a proper positioning of said spot 32' has been achieved. The reason for this is that the illuminating laser light fully couples into the elliptical-shaped central offtake bundle 47 in this position.

In the coarse-positioning step, at first the beam moving device 20 scans the flow cell 22 in the vertical direction range with the laser beam 32, or rather its spot 32', in given steps within the entire beam displacement range. When at least a portion of said spot 32' strikes the bundle 47, an electrical signal (e.g. a voltage signal) is generated in the output channel associated with said bundle 47. Scanning with the laser beam 32 is continued until the value of said voltage increases. When a (local) voltage maximum is exceeded, the beam moving device 20 continues the vertical scanning with the laser beam 32 but in a direction opposite to the scanning direction used so far and in smaller steps until said voltage reaches or exceeds a further (local) maximum. Now, the scanning direction turns about again and said scanning is continued in yet smaller steps until the next (local) voltage maximum is reached. This iterative scanning in the vertical direction is continued by the beam moving device 20 until the difference between two consecutive voltage maxima becomes smaller than a preset value (typically 0.5-1%). When said preset value is reached, vertical adjustment of the laser beam 32 is considered to be completed. Then, horizontal positioning of the laser beam 32 (spot 32') comes which is performed by an iterative process similar to the one applied in vertical positioning. Naturally, the coarse-positioning step can be started with a horizontal adjustment as well.

If the correct position in one of the directions is already known, coarse-positioning of the laser beam 32 (spot 32') in the other direction—instead of the previously discussed iterative process—can be realized by a single scanning with the beam in suitably tiny steps within the entire beam displacement range available in the direction concerned along with the simultaneous determination/recording of the voltage value obtained in each step, and then by a simple search for the (global) maximum of the data recorded; the latter could be performed e.g. by the control unit 56.

It is noted that the coarse-positioning of the laser beam 32, and thus the spot 32', takes place similarly in the arrangement that uses the masking plate 46 instead of the central bundle 47. In such a case, the only difference is that instead of voltage maxima, (local or global) voltage minima must be taken into account.

At the end of coarse-positioning, the spot 32' of the laser beam 32 covers the flow cell 22, however, its position relative to it is not necessarily optimal. In the fine-positioning step, horizontal position of the laser beam 32 must be adjusted with an accuracy of 5-10 μm. In the fine-positioning step, the spot 32' scans the cross-section of the flow cell 22 horizontally, the laser light scattered by the calibration object 40 is delivered via the optical fiber bundle to the respective sensing element(s), and after being digitized, the signal processing unit determines in a time frame of 10-500 ms the time average of peak values of the pulses generated. Then, the beam moving device 20 displaces the laser beam 32 (spot 32') until a short time average of peak values of the pulses generated reaches a maximum. To search the accurate position, the iterative process discussed previously is applied.

The automated position occupation by the laser beam 32 makes the manual adjustment of the optical unit in a cytometer according to the present invention unnecessary and requires no related skills from the user. Furthermore, the automated beam positioning allows a more precise adjustment and, hence, the noise due to a non-uniform illumination decreases and the signal-to-noise ratio improves. Moreover, said automated position occupation can equally be used to check the adequacy of the laser beam and the optical elements applied. The total beam cross-section can be tested through a single horizontal scanning performed in the entire beam displacement range: if the power density distribution within a central region of at most 30-60 μm in size of the laser beam's cross-section perpendicular to the propagation direction is not uniform enough (that is, its variations due to e.g. the contamination of the optical elements are greater than 1%), the optical unit of the cytometer according to the invention requires maintenance, and a notice of appropriate content is given the user.

In summary: in the case of an optical flow cytometer according to the present invention discussed merely with reference to some preferred embodiments but to such an extent that allows a full understanding of its operation, collection of light scattered by a sample to be assayed, in particular by formed elements in a sample of human or animal whole blood, and its transmission to the sensing element(s) take place by a coupling element of a particular construction, preferably by an optical fiber bundle made of elementary optical fibers through bonding or sintering and formed (preferably by grinding) with a desired geometry at the end thereof used to couple the light into it;

feeding, mixing and the tempered reaction of a sample to be assayed, in particular of a sample of human or animal whole blood, and the reagents required to perform the assay itself are accomplished in a particular sample preparation unit, wherein said sample preparation unit comprises a microreactor with a volume proportional to the incubation time, a temperature stabilizing member for adjusting the temperature of the desired reaction, and a mixer unit inducing—without disintegrating said microreactor—laminar and turbulent sections one after the other in a liquid flow that is advanced by pressure difference or reagent pump;

during the assay and feeding, the advancement of the sample prepared, in particular of the sample of human or animal whole blood, takes place in a specific hydro-pneumatical device, wherein the blood sample advances in the flow cell a given sample flow cross-section due to the pressure difference between the starting point and the end point of the liquid flow path, wherein said sample flow cross-section is defined by a ratio of the flow impedance of the sample branch to that of the sheath liquid branch;

during the assay, positioning of the laser light irradiating the sample prepared, in particular the sample of human or animal whole blood, onto said sample takes place in an automated manner, wherein the illuminating laser beam is adjusted horizontally and vertically by means of a calibrating sample flow so as to provide, on the one hand, the most uniform possible illumination of the formed elements in the sample flow and on the other hand to minimize the proportion of said laser beam directly striking the sensing element(s); and decreasing the proportion of laser light illuminating the sample that enters the sensing element is achieved by a flow cell of particular design.

The invention claimed is:

1. An optical flow cytometer to assay in vitro cellular components in a liquid sample, characterized in that said cytometer comprises a flow path extending from a starting point to an end point with a flow direction pointing from said starting point towards said end point, wherein
the starting point is formed by a first container for storing an auxiliary liquid at a first pressure, the end point is formed by a second container at a second pressure lower than said first pressure;

said flow path is composed of first and second flow branches formed so as to be capable of transporting said auxiliary liquid from the starting point to the end point, a unifying member (66) is inserted into the flow path that combines the flow branches into a common section and is capable of hydrodynamical focusing, wherein said common section is formed with a given cross-sectional area;

reactors are arranged between the starting point and the unifying element (66) in said first flow branch, said reactors are connected to one another so as to effect transportation in the flow direction, said reactors form parts of separate reagent branches (68-k) of the first flow branch for feeding the sample with cellular components and liquid phase reagents into the first flow branch and said reactors are formed so as to perform one or more reactions of the fed sample with the fed reagents in a controlled way and to transport the thus obtained prepared sample in the flow direction; and wherein the cross-sectional area is divided into cross-sectional areas of constituent flows of a composite stream according to the ratio of flow impedances of said first and second flow branches, wherein said composite stream is a layered stream composed of the auxiliary liquid and the prepared sample that enter said common section via the second and first flow branches, respectively, combined by said unifying member (66) through hydrodynamical focusing exerted by the unifying member (66) such that the composite stream allows passing of one cellular component of said sample at a time and flows in said common section laminarly in the flow direction due to the pressure difference prevailing between the starting point and the end point of the flow path;

a device to illuminate the common section by a shaped coherent beam of light in a given zone thereof from a direction essentially perpendicular to the extension of said common section;

an optical coupling element capable of collecting beams exiting from the illuminated zone of the common section in a first spatial distribution and transmitting said beams in a spatial distribution identical with said spatial distribution to a sensing surface of at least one optical sensing element $(A_1, \ldots, A_p)$, wherein said illumination device and said optical coupling element exhibit a common optical axis;

the at least one sensing element $(A_1, \ldots, A_p)$ is capable of generating at least one electrical signal in conformity with the spatial distribution of the beams incident on said sensing surface, each electric signal being proportional to the detected intensity of a respective incident beam;

a signal processing unit (54) electrically connected with the at least one optical sensing element $(A_1, \ldots, A_p)$ and being capable of processing the at least one electric signal generated by the at least one sensing element $(A_1, \ldots, A_p)$; and a controlling and evaluating unit electrically connected with an output of said signal processing unit (54) and capable of at least one of determining properties of the cellular components in the sample based on at least a part of the electrical signals processed and positioning said beam emitted by the illumination device onto the given zone of the common section by employing a part of the electrical signals processed as control parameters.

2. The flow cytometer according to claim 1, characterized in that the optical coupling element is an optical fiber bundle (24) assembled from elementary optical fibers (44) with geometrical axes parallel to one another, said optical fiber bundle (24) comprising a frontal end (42) facing the common section and formed with a surface capable of coupling beams propagating in said first spatial distribution into the elementary optical fibers (44); and offtake bundles (24-1, ..., 24-p) the sensing surface of the at least one sensing element $(A_1, \ldots, A_p)$ and formed with surfaces capable of coupling said beams coupled into the optical fibers (44) out of said elementary optical fibers (44) sorted as per specified regions of said spatial distribution, wherein each offtake bundle (24-1, ..., 24-p) is formed by a separate group of elementary optical fibers (44).

3. The flow cytometer according to claim 2, characterized in that the incoupling surface of the common end (42) is formed as one of (i) a plane surface perpendicular to the optical axis;

(ii) a spherical surface with a radius of about half of the distance between the centerline of the common section and the optical fiber bundle (24) measured along the optical axis; and (iii) an aspherical surface.

4. The flow cytometer according to claim 2, characterized in that the sensing surface of said at least one sensing element $(A_1, \ldots, A_p)$ is composed of more than one sensing surface portions, wherein each sensing surface portion is in optical coupling with a respective bundle (24-1, ..., 24-p) of the optical fiber bundle (24), and for each sensing surface portion/bundle pair, the bundle having a cross-sectional area larger than that of the respective sensing surface portion is formed with a spherical or aspherical outcoupling surface, while the bundle having a cross-sectional area of at most the same size as that of the respective sensing surface portion is formed with a plane outcoupling surface which is perpendicular to the geometrical axes of the optical fibers (44) forming the bundle concerned.

5. The flow cytometer according to claim 1, 4, characterized in that the specified regions of said spatial distribution are formed by a first spatial region of beams exiting said illuminated zone of the common section in parallel with the optical axis, and a second spatial region located between the conical angle range forming an angle of about 1.5° with the optical axis and the conical angle range forming an angle of about 3.0° with the optical axis, and a third spatial region located between the conical angle range forming an angle of about 4.0° with the optical axis and the conical angle range forming an angle of about 8.0° with the optical axis.

6. The flow cytometer according to claim 5, characterized in that an element impeding free passing on a beam coming from the first spatial region is arranged on the frontal end (42) of said optical fiber bundle (24).

7. The flow cytometer according to claim 6, characterized in that said element is provided by a masking element (46) that is non-transmissive with respect to beams striking thereon, is arranged on the frontal end (42) symmetrically with respect to the optical axis, and extends the full width of the optical fiber bundle (24) and the height of said first spatial region.

8. The flow cytometer according to claim 6, characterized in that said element is provided by an elliptical shaped central offtake bundle (47) of the optical fiber bundle (24) which is symmetrical with respect to the optical axis.

9. The flow cytometer according to claim 1, characterized in that said common section is at least partially formed by a flow cell (22, 22', 22", 22''') extending in the flow direction to a point of said flow path located downstream of the illumination zone and comprising a flow passage (22a, 22a', 22a", 22a''') that at least partially forms said flow path.

10. The flow cytometer according to claim 9, characterized in that those portions of the flow cell (22', 22", 22''') which—in plane sections of the flow cell (22', 22", 22''') essentially perpendicular to the optical axis—are located outside of a domain defined by the orthogonal projection of the flow passage (22a', 22a", 22a''') onto said plane sections, are formed so as to impede total passing of the illuminating beam through said flow cell (22', 22", 22''').

11. The flow cytometer according to claim 1, characterized in that a beam moving device (20) is arranged between the illumination device and the common section in the path of the illuminating beam, wherein said beam moving device (20) is electrically connected with the controlling and evaluating unit and is capable of positioning said beam in the common section onto the given illumination zone.

12. The flow cytometer according to claim 11, characterized in that said beam moving device (20) is composed of two antiparallel small angle prisms (34a, 34b) that can be rotated together and/or relative to each other around the optical axis.

13. The flow cytometer according to claim 11, characterized in that said beam moving device (20) is provided by the holder of the illumination device, wherein said holder is formed so as to be tiltable in the beam propagation direction around an axis essentially perpendicular to the optical axis up to a preset maximum angle.

14. The flow cytometer according to claim 1, characterized in that the reactors are microreactors (83, 83') with resilient walls, at least a part of said walls are arranged within the inner volume of a mixer unit (80) fully containing the walls so as to conform to the surface of the inner volume, and said inner volume of the mixer unit (80) is composed of sections arranged one after the other in fluid communication with one another and having different flow-through cross-sections.

15. The flow cytometer according to claim 14, characterized in that said mixer unit (80) is of modular construction, wherein all the modules are provided by individual clamping elements (82, 82') with inner structures creating said sections of different flow-through cross-sections.

16. The flow cytometer according to claim 1, characterized in that said illumination device is provided by a laser source (26) capable of emitting monochromatic laser light.

17. The flow cytometer according to claim 1, characterized in that said cellular components are provided by formed elements of human or animal whole blood.

18. A method of in vitro optical assaying of cellular components in a liquid sample, characterized by the steps of
feeding an auxiliary liquid into a flow path extending between a starting point and an end point at said starting point, said flow path being composed of first and second flow branches with a common section, maintaining at said starting point a first pressure and at said end point a second pressure in the meantime, said second pressure being lower than said first pressure;
feeding separately a sample to be assayed and reagents into said first flow branch at different points of this flow branch along with stopping feeding of the auxiliary liquid into the first flow branch;
mixing up and reacting the sample fed and the reagents by flowing those towards the common section in the first flow branch and creating thereby a homogeneous sample solution;
before entering said common section, subjecting said sample solution to a hydrodynamical focusing by means of the auxiliary liquid flow from said second flow branch, thereby preparing a composite stream flowing laminarly, said composite stream being composed of an inner fluid stream of the sample solution with a first cross-sectional area transporting the cellular components one by one after the other and an outer fluid stream of the auxiliary liquid surrounding said inner liquid stream as a sheath with a second cross-sectional area, wherein a ratio of the first cross-sectional area to the second cross-sectional area being adjusted by the flow impedances represented by said first and second flow branches;
while maintaining the laminar flow of the composite stream, feeding said stream into the common section and directing it therethrough, along with illuminating it in consecutive portions containing one cellular component at a time from a direction essentially perpendicular to the flow direction thereof;
directing light beams scattered by the cellular component in each consecutive portion of said composite stream to at least one optical sensing element ($A_1, \ldots, A_p$) along with keeping unaltered the scattering distribution of said light beams and generating at least one electrical signal proportional to the detected intensities of the incident light beams for each consecutive portion of the stream by means of the at least one optical sensing element;
processing the thus obtained electrical signal(s) and determining properties related to the cellular components in the sample based on at least a part of said electrical signal(s).

19. The method according to claim 18, characterized in that said scattered beams are led to the at least one optical sensing element ($A_1, \ldots, A_p$) by means of an optical coupling element.

20. The method according to claim 18, characterized in that said auxiliary liquid, said sample and said reagents fed into the flow branches are kept in flow by a pressure difference prevailing between said starting and end points.

21. The method according to claim 18, characterized in that said sample and said reagents are fed into the first flow branch and kept in flow in said flow branch by reagent pumps (69-1, . . . , 69-n) connected to feed-in points of said flow branch.

22. The method according to claim 18, characterized in that the composite stream is created and then kept in flowing by the pressure difference prevailing between said starting and end points.

23. The method according to claim 18, characterized in that the mix-up and the reactions of the sample and the reagents are performed in reactors under temperature control, each reactor being inserted into between two feed-in points, wherein the lengths of said reactors are selected so as to allow taking place of the reaction between said sample and said reagents to a desired extent.

24. The method according to claim 18, characterized in that to provide the most uniform possible illumination of the cellular components, the light beam used to illuminate the composite stream is subjected to beam forming, as well as to positioning consisting of a coarse-positioning step and a subsequent fine-positioning step, said positioning is performed iteratively and repeatedly by means of exploiting at least a part of said electrical signals processed as control parameters until reaching a preset threshold condition.

25. The method according to claim 24, characterized in that a laser beam (32) illuminating the composite stream flowing through the common section in an elliptical spot (32') with a Gaussian power density distribution is used as said light beam subjected to beam shaping and positioning.

26. The method according to claim 25, characterized in that in the coarse-positioning step, an electrical signal generated by a portion of said illuminating laser beam (32) that reaches said optical sensing element ($A_1, \ldots, A_p$) without being scattered is made use of as the control parameter.

27. The method according to claim 25, characterized in that in the fine-positioning step, a composite stream comprising calibration objects (40) similar to the cellular components to be assayed as to their physical properties is led through said common section and one or more electrical signals generated by one or more portions of said illuminating laser beam (32) that reach said optical sensing element ($A_1, \ldots, A_p$) and being scattered by these objects (40) are made use of as the control parameter.

28. The method according to claim 27, characterized in that formed elements of human or animal whole blood or microballs with the same size as that of said formed elements are used as the calibration objects (40).

* * * * *